(12) United States Patent
Andersen

(10) Patent No.: US 7,066,914 B2
(45) Date of Patent: *Jun. 27, 2006

(54) CATHETER HAVING A TIP WITH AN ELONGATED COLLAR

(75) Inventor: Erik Andersen, Gurnee, IL (US)

(73) Assignee: Bird Products Corporation, Conshocken, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/081,153

(22) Filed: Mar. 16, 2005

(65) Prior Publication Data

US 2005/0159712 A1    Jul. 21, 2005

Related U.S. Application Data

(63) Continuation of application No. 10/315,742, filed on Dec. 9, 2002, now Pat. No. 6,878,143, which is a continuation of application No. 09/614,360, filed on Jul. 12, 2000, now Pat. No. 6,511,474.

(51) Int. Cl.
*A61M 31/00* (2006.01)

(52) U.S. Cl. ............ 604/270; 604/264; 604/268; 604/910

(58) Field of Classification Search ........... 604/264, 604/268, 270, 516, 910
See application file for complete search history.

(56) References Cited

U.S. PATENT DOCUMENTS

| | | |
|---|---|---|
| 803,469 A | 10/1905 | Cilley et al. |
| 910,125 A | 1/1909 | Graser |
| 1,211,928 A | 1/1917 | Fisher |
| 1,242,174 A | 10/1917 | Gouch |
| 1,335,672 A | 3/1920 | DuNouy |
| 1,380,991 A | 6/1921 | Collins |
| 1,417,141 A | 5/1922 | Carter |
| 1,615,873 A | 2/1927 | Fitch |
| 1,635,373 A | 7/1927 | Lofholm |
| 1,696,763 A | 12/1928 | Hare |
| 1,736,182 A | 11/1929 | Wilkins |
| 1,767,073 A | 6/1930 | Ingold |
| 1,865,926 A | 7/1932 | Laing |
| 1,879,249 A | 9/1932 | Honsaker |
| 1,888,349 A | 11/1932 | Jacoby |
| 1,899,781 A | 2/1933 | Twiss |
| 1,903,681 A | 4/1933 | Merliss |
| 2,116,083 A | 5/1938 | Rusch |
| 2,218,285 A | 10/1940 | Jellik, Jr. |
| 2,409,343 A | 10/1946 | Curtis |
| 2,491,516 A | 12/1949 | Piggot et al. |
| 2,626,855 A | 1/1953 | Hand |

(Continued)

FOREIGN PATENT DOCUMENTS

AU        642647      10/1993

(Continued)

OTHER PUBLICATIONS

"Corscope Endoscopically Placed Feeding Tube" brochure, copyright 1992, on or before December thereof.

(Continued)

*Primary Examiner*—Thomas Denion
*Assistant Examiner*—Ching Chang
(74) *Attorney, Agent, or Firm*—Bell, Boyd & Lloyd, LLC

(57) ABSTRACT

A catheter having a tube and a tip connected to one end of the tube. The tip has a collar, an end member and lowered side walls positioned between the collar and the end member. The lowered side walls define an opening that is biased toward the end member.

24 Claims, 3 Drawing Sheets

U.S. PATENT DOCUMENTS

| | | |
|---|---|---|
| 2,671,028 A | 3/1954 | Clark |
| 2,694,984 A | 11/1954 | Daniels |
| 2,699,167 A | 1/1955 | Raiche |
| 2,717,598 A | 9/1955 | Krasno |
| 2,731,053 A | 1/1956 | Lockhart |
| 2,735,432 A | 2/1956 | Hudson |
| 2,816,692 A | 12/1957 | Schade |
| 2,817,372 A | 12/1957 | Barr, Sr. et al. |
| 2,935,067 A | 5/1960 | Bouet |
| 2,957,196 A | 10/1960 | Kreider et al. |
| 2,961,691 A | 11/1960 | Roy et al. |
| 2,969,063 A | 1/1961 | Broman |
| 2,986,142 A | 5/1961 | Bieberdorf et al. |
| 2,999,387 A | 9/1961 | Andelin |
| 3,001,525 A | 9/1961 | Hendricks |
| 3,067,015 A | 12/1962 | Lawdermilt |
| 3,087,493 A | 4/1963 | Schossow |
| 3,090,532 A | 5/1963 | Robson |
| 3,092,106 A | 6/1963 | Butler |
| D196,611 S | 10/1963 | Alder et al. |
| 3,108,717 A | 10/1963 | Kindseth |
| 3,189,031 A | 6/1965 | Andersen |
| 3,190,291 A | 6/1965 | Foley |
| 3,229,678 A | 1/1966 | Anspach |
| 3,239,096 A | 3/1966 | Buono et al. |
| 3,239,104 A | 3/1966 | Scholle |
| 3,241,554 A | 3/1966 | Coanda |
| 3,253,594 A | 5/1966 | Matthews et al. |
| 3,288,332 A | 11/1966 | Etter et al. |
| 3,311,267 A | 3/1967 | Lee et al. |
| 3,311,268 A | 3/1967 | Fields |
| 3,346,464 A | 10/1967 | Ernst |
| 3,373,735 A | 3/1968 | Gallagher |
| 3,395,710 A | 8/1968 | Stratton et al. |
| 3,395,711 A | 8/1968 | Plzak, Jr. |
| 3,548,805 A | 12/1970 | Datsenko et al. |
| 3,568,679 A | 3/1971 | Reif |
| 3,593,713 A | 7/1971 | Bogoff |
| 3,597,124 A | 8/1971 | Adams |
| 3,640,282 A | 2/1972 | Kamen et al. |
| 3,648,703 A | 3/1972 | Manker |
| 3,656,485 A | 4/1972 | Robertson |
| 3,664,339 A | 5/1972 | Santomieri |
| 3,683,911 A | 8/1972 | McCormick |
| 3,709,211 A | 1/1973 | Hawkins |
| 3,771,527 A | 11/1973 | Ruisi |
| 3,782,388 A | 1/1974 | Page |
| 3,799,173 A | 3/1974 | Kamen |
| 3,831,587 A | 8/1974 | Boyd |
| 3,856,020 A | 12/1974 | Kovac |
| 3,880,311 A | 4/1975 | McPhee |
| 3,881,254 A | 5/1975 | Epstein |
| 3,889,685 A | 6/1975 | Miller, Jr. et al. |
| 3,902,932 A | 9/1975 | Gdanski et al. |
| 3,915,212 A | 10/1975 | Bujan et al. |
| 3,929,126 A | 12/1975 | Corsaut |
| 3,985,135 A | 10/1976 | Carpenter |
| 4,007,740 A | 2/1977 | Owen |
| 4,020,829 A | 5/1977 | Willson et al. |
| 4,025,241 A | 5/1977 | Clemens |
| 4,027,659 A | 6/1977 | Slingluff |
| 4,057,065 A | 11/1977 | Thow |
| 4,058,121 A | 11/1977 | Choksi et al. |
| 4,072,146 A | 2/1978 | Howes |
| 4,076,285 A | 2/1978 | Martinez |
| 4,085,866 A | 4/1978 | Fekl |
| 4,114,625 A | 9/1978 | Onat |
| 4,141,364 A | 2/1979 | Schultze |
| 4,148,319 A | 4/1979 | Kasper et al. |
| 4,173,228 A | 11/1979 | Van Steenwyk et al. |
| 4,176,662 A | 12/1979 | Frazer |
| 4,185,948 A | 1/1980 | Maguire |
| 4,187,893 A | 2/1980 | BuJan |
| 4,198,971 A | 4/1980 | Noiles |
| 4,201,208 A | 5/1980 | Cambio, Jr. |
| 4,211,519 A | 7/1980 | Hogan |
| 4,229,299 A | 10/1980 | Savitz et al. |
| 4,230,123 A | 10/1980 | Hawkins, Jr. |
| 4,232,421 A | 11/1980 | Tucker |
| 4,257,416 A | 3/1981 | Prager |
| 4,257,421 A | 3/1981 | Beal |
| 4,257,748 A | 3/1981 | Ives et al. |
| 4,259,952 A | 4/1981 | Avoy |
| 4,261,363 A | 4/1981 | Russo |
| 4,269,332 A | 5/1981 | Conn |
| 4,270,542 A | 6/1981 | Plumley |
| 4,282,863 A | 8/1981 | Beigler et al. |
| 4,288,205 A | 9/1981 | Henk |
| 4,296,949 A | 10/1981 | Muetterties et al. |
| 4,298,045 A | 11/1981 | Weiler et al. |
| 4,311,140 A | 1/1982 | Bridgman |
| 4,315,513 A | 2/1982 | Nawash et al. |
| 4,323,065 A | 4/1982 | Kling |
| 4,344,434 A | 8/1982 | Robertson |
| 4,346,703 A | 8/1982 | Dennehey et al. |
| 4,349,024 A | 9/1982 | Ralston, Jr. |
| 4,354,492 A | 10/1982 | McPhee |
| 4,356,824 A | 11/1982 | Vazquez |
| 4,364,394 A | 12/1982 | Wilkinson |
| 4,381,011 A | 4/1983 | Somers, III |
| 4,388,076 A | 6/1983 | Waters |
| 4,390,017 A | 6/1983 | Harrison et al. |
| 4,392,853 A | 7/1983 | Muto |
| 4,392,855 A | 7/1983 | Oreopoulos |
| 4,393,873 A | 7/1983 | Nawash et al. |
| 4,405,316 A | 9/1983 | Mittleman |
| 4,410,320 A | 10/1983 | Dykstra |
| 4,411,656 A | 10/1983 | Cornett, III |
| 4,411,661 A | 10/1983 | Kersten |
| 4,416,289 A | 11/1983 | Bresler |
| 4,419,094 A | 12/1983 | Patel |
| 4,432,763 A | 2/1984 | Manschot et al. |
| 4,435,174 A | 3/1984 | Redmond et al. |
| 4,439,188 A | 3/1984 | Dennehey et al. |
| 4,449,974 A | 5/1984 | Messingschlager |
| 4,464,175 A | 8/1984 | Altman et al. |
| 4,472,116 A | 9/1984 | Wenstrup |
| 4,473,094 A | 9/1984 | Harris |
| 4,479,274 A | 10/1984 | Biby |
| 4,484,916 A | 11/1984 | McPhee |
| 4,490,143 A | 12/1984 | Quinn et al. |
| 4,496,295 A | 1/1985 | King |
| 4,496,347 A | 1/1985 | MacLean et al. |
| 4,498,843 A | 2/1985 | Schneider et al. |
| 4,515,584 A | 5/1985 | Abe et al. |
| 4,516,968 A | 5/1985 | Marshall et al. |
| 4,516,970 A | 5/1985 | Kaufman et al. |
| 4,518,327 A | 5/1985 | Hackman |
| 4,521,212 A | 6/1985 | Ruschke |
| 4,529,102 A | 7/1985 | Quinn et al. |
| 4,531,943 A | 7/1985 | Van Tassel et al. |
| 4,543,089 A | 9/1985 | Moss |
| 4,552,554 A | 11/1985 | Gould et al. |
| 4,553,971 A | 11/1985 | Ashley et al. |
| 4,559,046 A | 12/1985 | Groshong et al. |
| 4,569,675 A | 2/1986 | Prosl et al. |
| 4,573,576 A | 3/1986 | Krol |
| 4,574,173 A | 3/1986 | Bennett |
| 4,580,573 A | 4/1986 | Quinn |
| D284,035 S | 5/1986 | DeLeeuwe et al. |
| 4,588,396 A | 5/1986 | Stroebel et al. |
| 4,588,402 A | 5/1986 | Igari et al. |
| 4,594,074 A * | 6/1986 | Andersen et al. ............ 604/270 |
| 4,598,699 A | 7/1986 | Garren et al. |

| | | | | | |
|---|---|---|---|---|---|
| 4,607,868 A | 8/1986 | Harvey et al. | 4,946,440 A | 8/1990 | Hall |
| 4,610,673 A | 9/1986 | Russo | 4,950,254 A | 8/1990 | Andersen et al. |
| 4,613,323 A | 9/1986 | Norton et al. | 4,958,634 A | 9/1990 | Jang |
| 4,639,019 A | 1/1987 | Mittleman | 4,959,055 A | 9/1990 | Hillyer |
| 4,642,092 A | 2/1987 | Moss | 4,961,430 A | 10/1990 | Sheahon |
| 4,645,492 A | 2/1987 | Weeks | 4,963,132 A | 10/1990 | Gibson |
| 4,654,036 A | 3/1987 | Tolkoff | 4,963,133 A | 10/1990 | Whipple |
| 4,655,763 A | 4/1987 | Malcolm et al. | 4,966,583 A | 10/1990 | Debbas |
| 4,666,433 A | 5/1987 | Parks | 4,969,879 A | 11/1990 | Lichte |
| 4,668,222 A | 5/1987 | Poirier | 4,973,329 A | 11/1990 | Park et al. |
| 4,668,225 A | 5/1987 | Russo | 4,976,691 A | 12/1990 | Sahota |
| 4,673,334 A | 6/1987 | Allington et al. | 4,976,703 A | 12/1990 | Franetzki et al. |
| 4,676,782 A | 6/1987 | Yamamoto et al. | 4,981,482 A | 1/1991 | Ichikawa |
| 4,681,564 A | 7/1987 | Landreneau | 4,986,807 A | 1/1991 | Farr |
| 4,683,916 A | 8/1987 | Raines | 4,990,139 A | 2/1991 | Jang |
| 4,684,038 A | 8/1987 | Gaul et al. | 4,991,629 A | 2/1991 | Ernesto et al. |
| 4,685,901 A | 8/1987 | Parks | 4,994,033 A | 2/1991 | Shockey et al. |
| 4,685,912 A | 8/1987 | Jones | 4,994,048 A | 2/1991 | Metzger |
| 4,687,470 A | 8/1987 | Okada | 5,007,900 A | 4/1991 | Picha et al. |
| 4,687,471 A | 8/1987 | Twardowski et al. | 5,017,188 A | 5/1991 | Marten et al. |
| 4,690,138 A | 9/1987 | Heyden | 5,026,352 A | 6/1991 | Anderson |
| 4,692,152 A | 9/1987 | Emde | 5,037,387 A | 8/1991 | Quinn et al. |
| 4,699,296 A | 10/1987 | Schrock, Jr. | 5,041,085 A | 8/1991 | Osborne et al. |
| 4,701,159 A | 10/1987 | Brown et al. | 5,044,369 A | 9/1991 | Sahota |
| 4,701,162 A | 10/1987 | Rosenberg | 5,047,021 A | 9/1991 | Utterberg |
| 4,701,163 A | 10/1987 | Parks | 5,049,139 A | 9/1991 | Gilchrist |
| 4,714,460 A | 12/1987 | Calderon | 5,057,091 A | 10/1991 | Andersen |
| 4,717,385 A | 1/1988 | Cameron | 5,057,093 A | 10/1991 | Clegg et al. |
| 4,721,115 A | 1/1988 | Owens | 5,059,170 A | 10/1991 | Cameron |
| 4,722,344 A | 2/1988 | Cambron et al. | 5,059,178 A | 10/1991 | Ya |
| 4,735,607 A | 4/1988 | Keith, Jr. | 5,061,256 A | 10/1991 | Wampler |
| 4,743,231 A | 5/1988 | Kay et al. | 5,073,166 A | 12/1991 | Parks et al. |
| 4,744,366 A | 5/1988 | Jang | 5,074,846 A | 12/1991 | Clegg et al. |
| 4,753,639 A | 6/1988 | Iwatschenko | 5,078,681 A | 1/1992 | Kawashima |
| 4,758,219 A | 7/1988 | Sacks | 5,078,743 A | 1/1992 | Mikalov et al. |
| 4,762,519 A | 8/1988 | Frimberger | D324,566 S | 3/1992 | Schmidt et al. |
| 4,769,014 A | 9/1988 | Russo | 5,092,847 A | 3/1992 | Pozzo |
| 4,772,269 A | 9/1988 | Twardowski et al. | 5,092,850 A | 3/1992 | Buma |
| 4,774,940 A | 10/1988 | Linder | 5,098,405 A | 3/1992 | Peterson et al. |
| 4,778,455 A | 10/1988 | Kousai et al. | 5,108,368 A | 4/1992 | Hammerslag et al. |
| 4,778,477 A | 10/1988 | Lauchenauer | 5,112,310 A | 5/1992 | Grobe |
| 4,779,611 A | 10/1988 | Grooters et al. | 5,125,897 A | 6/1992 | Quinn et al. |
| 4,781,704 A | 11/1988 | Potter | 5,147,308 A | 9/1992 | Singer |
| 4,787,890 A | 11/1988 | Ufermann | 5,149,330 A | 9/1992 | Brightbill |
| 4,795,430 A | 1/1989 | Quinn et al. | 5,151,086 A | 9/1992 | Duh et al. |
| 4,795,446 A | 1/1989 | Fecht | 5,152,749 A | 10/1992 | Giesy et al. |
| 4,798,593 A | 1/1989 | Iwatschenko | 5,152,756 A | 10/1992 | Quinn et al. |
| 4,798,605 A | 1/1989 | Steiner et al. | 5,156,596 A | 10/1992 | Balbierz et al. |
| 4,811,737 A | 3/1989 | Rydell | 5,167,627 A | 12/1992 | Clegg et al. |
| 4,820,270 A | 4/1989 | Hardcastle et al. | 5,171,216 A | 12/1992 | Dasse et al. |
| 4,820,288 A | 4/1989 | Isono | 5,207,648 A | 5/1993 | Gross |
| 4,822,338 A | 4/1989 | Longmore et al. | 5,211,165 A | 5/1993 | Dumoulin et al. |
| 4,824,435 A | 4/1989 | Giesy et al. | D338,726 S | 8/1993 | Andersen et al. |
| 4,826,481 A | 5/1989 | Sacks et al. | 5,231,989 A | 8/1993 | Middleman et al. |
| 4,832,584 A | 5/1989 | Nassif | 5,231,994 A | 8/1993 | Harmjanz |
| 4,834,712 A | 5/1989 | Quinn et al. | 5,234,417 A | 8/1993 | Parks et al. |
| 4,834,713 A | 5/1989 | Suthanthiran | 5,250,040 A | 10/1993 | Parks et al. |
| 4,834,732 A | 5/1989 | Steer et al. | 5,263,944 A | 11/1993 | Vidal et al. |
| 4,838,881 A | 6/1989 | Bennett | 5,267,968 A | 12/1993 | Russo |
| 4,854,330 A | 8/1989 | Evans, III et al. | 5,267,969 A | 12/1993 | Hirsch et al. |
| 4,860,742 A | 8/1989 | Park et al. | 5,267,970 A | 12/1993 | Chin et al. |
| 4,863,424 A | 9/1989 | Blake et al. | 5,284,474 A | 2/1994 | Adair |
| 4,863,438 A | 9/1989 | Gauderer et al. | 5,290,282 A | 3/1994 | Casscells |
| 4,867,742 A | 9/1989 | Calderon | 5,303,714 A | 4/1994 | Abele et al. |
| 4,895,275 A | 1/1990 | Quinn et al. | 5,305,742 A | 4/1994 | Styers et al. |
| 4,900,306 A | 2/1990 | Quinn et al. | 5,308,325 A | 5/1994 | Quinn et al. |
| 4,904,238 A | 2/1990 | Williams | 5,318,543 A | 6/1994 | Ross et al. |
| 4,905,698 A | 3/1990 | Strohl, Jr. et al. | 5,336,203 A | 8/1994 | Goldhardt et al. |
| 4,921,138 A | 5/1990 | Quinn et al. | 5,342,321 A | 8/1994 | Potter |
| 4,929,236 A | 5/1990 | Sampson | 5,356,382 A | 10/1994 | Picha et al. |
| 4,935,004 A | 6/1990 | Cruz | 5,356,391 A | 10/1994 | Stewart |
| 4,943,275 A | 7/1990 | Stricker | 5,374,251 A | 12/1994 | Smith |
| 4,944,732 A | 7/1990 | Russo | 5,374,254 A | 12/1994 | Buma |

| | | | | | |
|---|---|---|---|---|---|
| 5,385,561 A | 1/1995 | Cerny | DE | 8705894 | 7/1987 |
| 5,391,159 A | 2/1995 | Hirsch et al. | DE | 19830183 | 1/1999 |
| 5,399,173 A | 3/1995 | Parks et al. | EP | 0102342 | 3/1984 |
| 5,421,819 A | 6/1995 | Edwards et al. | EP | 0160395 | 11/1985 |
| 5,423,764 A | 6/1995 | Fry | EP | 0182539 | 5/1986 |
| 5,431,640 A | 7/1995 | Gabriel | EP | 0256546 | 2/1988 |
| 5,433,722 A | 7/1995 | Sharpe et al. | EP | 1036570 | 9/2000 |
| 5,451,212 A | 9/1995 | Andersen | EP | 1311226 | 5/2003 |
| 5,451,216 A | 9/1995 | Quinn | FR | 0591963 | 7/1925 |
| 5,458,583 A | 10/1995 | McNeely et al. | FR | 0900765 | 7/1945 |
| 5,484,420 A | 1/1996 | Russo | FR | 1511044 | 1/1968 |
| 5,489,249 A | 2/1996 | Brewer et al. | FR | 2276483 | 1/1976 |
| 5,489,275 A | 2/1996 | Thompson et al. | FR | 565 491 | 6/1984 |
| 5,492,119 A | 2/1996 | Abrams | GB | 745379 | 2/1956 |
| 5,498,249 A | 3/1996 | Quinn | GB | 891754 | 3/1962 |
| 5,512,037 A | 4/1996 | Russell et al. | GB | 2067574 | 11/1997 |
| 5,545,141 A | 8/1996 | Eld | JP | 58-170869 | 10/1983 |
| 5,555,898 A | 9/1996 | Suzuki et al. | JP | 4092668 | 3/1992 |
| 5,556,385 A | 9/1996 | Andersen | WO | WO 90/03777 | 4/1990 |
| 5,571,093 A | 11/1996 | Cruz et al. | WO | WO 93/11823 | 6/1993 |
| 5,571,116 A | 11/1996 | Bolanos et al. | WO | WO 94/06636 | 3/1994 |
| 5,599,322 A * | 2/1997 | Quinn ........................ 604/270 | WO | WO 94/28953 | 12/1994 |
| 5,628,753 A | 5/1997 | Cracauer et al. | WO | WO 95/03733 | 2/1995 |
| 5,630,794 A | 5/1997 | Lax et al. | WO | WO 96/05768 | 2/1996 |
| 5,658,253 A | 8/1997 | Piontek et al. | WO | WO 96/07352 | 3/1996 |
| 5,665,064 A | 9/1997 | Bodicky et al. | WO | WO 97/29683 | 8/1997 |
| 5,676,674 A | 10/1997 | Bolanos et al. | WO | WO 03/043679 | 5/2003 |
| 5,716,347 A | 2/1998 | Gibbs et al. | WO | WO 2004/060437 | 7/2004 |
| 5,720,734 A | 2/1998 | Copenhaver et al. | | | |
| 5,727,553 A | 3/1998 | Saad | | | |
| 5,766,202 A | 6/1998 | Jones et al. | | | |
| 5,810,787 A | 9/1998 | Quinn | | | |
| 5,836,315 A | 11/1998 | Benderev et al. | | | |
| 5,851,195 A | 12/1998 | Gill | | | |
| 5,860,952 A | 1/1999 | Quinn | | | |
| 5,860,960 A | 1/1999 | Quinn | | | |
| 5,865,816 A | 2/1999 | Quinn | | | |
| 5,891,113 A | 4/1999 | Quinn | | | |
| 5,897,562 A | 4/1999 | Bolanos et al. | | | |
| 5,910,128 A | 6/1999 | Quinn | | | |
| 5,941,855 A | 8/1999 | Picha et al. | | | |
| 5,989,231 A | 11/1999 | Snow et al. | | | |
| 6,030,364 A | 2/2000 | Durgin et al. | | | |
| 6,036,673 A | 3/2000 | Quinn | | | |
| 6,039,714 A | 3/2000 | Cracauer et al. | | | |
| 6,066,112 A | 5/2000 | Quinn | | | |
| 6,077,243 A | 6/2000 | Quinn | | | |
| 6,077,250 A | 6/2000 | Snow et al. | | | |
| 6,090,073 A | 7/2000 | Gill | | | |
| 6,186,985 B1 | 2/2001 | Snow | | | |
| 6,322,495 B1 | 11/2001 | Snow et al. | | | |
| 6,322,538 B1 | 11/2001 | Elbert et al. | | | |
| 6,358,197 B1 * | 3/2002 | Silverman et al. ............ 600/29 | | | |
| 6,402,722 B1 | 6/2002 | Snow et al. | | | |
| 6,458,106 B1 | 10/2002 | Meier et al. | | | |
| 6,471,676 B1 | 10/2002 | DeLegge et al. | | | |
| 6,482,170 B1 | 11/2002 | Andersen | | | |
| 6,511,474 B1 | 1/2003 | Andersen | | | |
| 6,582,395 B1 | 6/2003 | Burkett et al. | | | |
| 6,878,143 B1 * | 4/2005 | Andersen ................... 604/264 | | | |
| 2003/0097099 A1 | 5/2003 | Quinn | | | |
| 2004/0087877 A1 | 5/2004 | Besz et al. | | | |

FOREIGN PATENT DOCUMENTS

| | | |
|---|---|---|
| CA | 2163622 | 12/1994 |
| CA | 2420676 | 2/2003 |
| CN | 1049288 | 2/1991 |
| DE | 1264317 | 3/1968 |
| DE | 2005167 | 2/1970 |
| DE | 2837265 | 3/1980 |
| DE | 3444909 A1 | 6/1986 |
| DE | 3611112 | 7/1987 |

OTHER PUBLICATIONS

"Silk Over-The Wire Jejunostomy Tube" brochure, copyright 1993, on or before December thereof.

"A New Technique for Jejunal Feeding Tube Placement: A Marriage of Enterscope and Laparascope," Etzkorn, Vitello, Resnick, McGuire, Venu and Watkins, Gastrointestinal Endoscopy, vol. 43, No. 6, pp. 610-613, 1996, on or before Dec. thereof.

"A Simplified Technique for Constructing A Tube Feeding Gastrostomy", Gauderer and Ponsky, Reprint from SURGERY, Gynecology & Obstetrics, Jan., 1981, vol. 152, pp. 82-85.

Children's Medical Ventures Feeding Tube photograph, prior to Sep. 7, 2005.

Children's Medical Ventures Extension Set for Feeding Tube photograph, prior to Sep. 7, 2005.

"Direct Percutaneous Endoscopic Jejunostomy", Blair S. Lewis, MD, Gastrointestinal Endoscopy, vol. 37, No. 4, 1991, p. 493, 1991, on or before Dec. thereof.

"Direct Percutaneous Endoscopic Jejunostomies", Shike, Wallach and Likier, Gastrointestinal Endoscopy, vol. 37, No. 1, 1991, pp. 62-65, 1991, on or before Dec. thereof.

Exacta-Med® Dispenser photograph, prior to Sep. 7, 2005.

"Gastrostomy Without Laparotomy: A Percutaneous Endoscopic Technique", Journal of Pediatric Surgery, vol. 15, No. 6 (Dec.), 1980, pp. 872-875.

IV Line photograph, prior to Sep. 7, 2005.

IV Syringe photograph, prior to Sep. 7, 2005.

Medicina™ Feeding Syringe photograph, prior to Jul., 2004.

Medicina™ Feeding Tube photograph, prior to Jul., 2004.

Medicina™ Extension Feeding Set photograph, prior to Jul., 2004.

"New and Emerging Techniques—Surgical Rapid Review, Percutaneous Endoscopic Sigmoid Colostomy", Australian Safety and Efficacy Register of New Interventional Procedures—Surgical, Jun. 2003.

"New Method of Percutaneous Gastrostomy Using Anchoring Devices", America Journal Of Surgery, Am J. Surg 1987; 153: pp. 230-232, Feb., 1987.

"Newsletter, newproductsupdate", published by Medicina prior to Jul., 2004.

"Pediatric Surgery for the Primary Care Pediatrician, Part II" from Pediatric Clinics of North America, vol. 45, No. 6, Dec., 1998.

"Percutaneous Endoscopic Jejunostomy In Cancer Patients With Previous Gastric Resection", Shike, Schroy, Ritchie, Lightdale and Morse, Gastrintestinal Endoscopy, vol. 33, No. 5, 1987, pp. 372-374, copyright 1987, on or before Dec. thereof.

"Prolonged Peritoneal Dialysis for Chronic Renal Failure", *The Lancet*, Mar. 28, 1964, pp. 700-702.

"Recurrent Sigmoid Volvulus Treated By Percutaneous Endoscopic Colostomy", written by I.R. Daniels, M.J. Lamparelli, H. Chave and J. N. L. Simson, British Journal of Surgery in the year 2000 in or before the month of Dec. thereof.

"The Application of Percutaneous Endoscopic colostomy to the Mangement of Obstructed Defecation", written by A. G. Heriot, M.D., H.S. Tilney, M.R.C.S. and J. N. L. Simson, M. Chir., from the Department of Colorectal Surgery, St. Richard's Hospital, Chichester, England, May 2002.

The Farrell Valve Enteral Gastric Pressure Relief System Advertisement, 1999 in or before the month of Dec. thereof.

VIASYS MedSystems™ Neonatal/Pediatric Feeding Tube photograph, prior to Sep. 7, 2005.

* cited by examiner

CATHETER HAVING A TIP WITH AN ELONGATED COLLAR

PRIORITY CLAIM

This application is a continuation of and claims priority to and the benefit of U.S. patent application Ser. No. 10/315, 742, filed Dec. 9, 2002, now U.S. Pat. No. 6,878,143, the disclosure of which is incorporated herein in its entirety, which is a continuation of U.S. patent application Ser. No. 09/614,360, filed Jul. 12, 2000, now U.S. Pat. No. 6,511,474.

CROSS REFERENCE TO RELATED APPLICATIONS

This application is related to the following commonly owned co-pending patent applications: "Bolus for Non-Occluding High Flow Enteral Feeding Tube," Ser. No. 10/315,742, (Referenced Above); and "Bolus for Non-Occluding High Flow Enteral Feeding Tube," Ser. No. 10/321, 337.

TECHNICAL FIELD

The present invention generally relates to the irrigation, administration and aspiration of fluids to and from body cavities such as the gastrointestinal tract through a catheter and, in particular, to an enteral feeding tube having a non-collapsible bolus containing a fluid opening disposed at a distal end of the tube.

BACKGROUND OF THE INVENTION

Enteral nutrition is a form of hyperalimentation and metabolic support in which nutrient formulas or medicaments are delivered directly to the gastrointestinal tract. Fluid administration and aspiration is accomplished through use of a nasogastrointestinal tube generally referred to as an enteral feeding tube, as shown in FIG. 1. Enteral feeding is frequently utilized where adequate nutritional intake cannot be achieved through oral alimentation because of poor appetite, chronic nausea, general apathy, sedation or other symptoms or characteristics associated with serious disease. By delivering appropriate nutrient fluids directly to the gastrointestinal tract through an enteral feeding tube, nutritional and metabolic support of the patient is achieved without risk of sepsis or metabolic derangement, which may occur in intraveneous hyperalimentation. Because of increasing emphasis on out-patient care, enteral nutrition has been recognized as a desirable method of hyperalimentation as it requires only oral intubation of the feeding tube rather than manipulation of sterile cannulae or other means of interconnection with surgically implanted subclavian catheters as used in parenteral hyperalimentation.

Prior art feeding tubes, or catheters, typically include a rigid tip, or bolus, that includes a fluid outlet that promotes fluid flow. The fluid outlet is typically provided through a sidewall of the bolus to guard against occlusion with mucous, gastrointestinal debris or coagulated feeding material. The bolus is also more rigid than the enteral tube so that the tube can be easily guided during the intubation procedure. The enteral tube may also be provided with a wire stylet within the tube to provide more rigidity to the tube during intubation. The stylet can then be removed when the tube is inserted to the desired position within the gastrointestinal tract. Inadvertent exiting of the stylet during intubation is reduced by positioning the fluid outlet within the sidewall of the bolus.

In some situations, the enteral tube is introduced into the gastrointestinal tract in an over-the-wire intubation procedure. This procedure requires a bolus having an open ended tip. A wire stylet, or guide wire, extends through the enteral tube and out the open end of the bolus tip. The guide wire is used to guide the enteral tube and bolus to a location that may be more difficult to reach. The guide wire provides more control over the tube and bolus for placement in these locations. For example, the guide wire may be used to guide the bolus and enteral tube through the stomach and into the jejunum or duodenum. The guide wire, which is relatively stiff compared to the enteral tube, is inserted ahead of the bolus to a desired position. The enteral tube is then slipped over the wire and advanced to the desired position. When the enteral tube is properly placed, the wire is removed.

One disadvantage in the prior art is that an over-the-wire intubation procedure typically requires a bolus having a different design than those used in other procedures. Prior art boluses for use in an over-the-wire procedure are typically open-ended tubes that do not incorporate a rounded tip. On the other hand, boluses used in other types of intubation procedures typically have a rounded or bullet-shaped tip that provides less resistance during intubation. These shaped tips also reduce the risk of internal injury. Thus, each bolus design facilitates the specific intubation procedure. Another disadvantage of prior art boluses is their susceptibility to bending and kinking at a collar portion of the bolus that connects to a distal end of the enteral tube. Since the enteral tube is made of a material that is typically more flexible than the bolus, kinking readily occurs at the joint between the materials of differing flexibility. These boluses are also susceptible to bending at the fluid opening, where there is less material to provide rigidity to the bolus. This bending and kinking makes controlled intubation more difficult. Furthermore, the bending and kinking of the collar portion may also cause problems when using a wire stylet. The overall lengths of the stylet and tube are subject to certain assembly tolerances. When the length of the stylet is within the shorter dimension range and the length of the tube is within the longer dimension range, the stylet may not reach the collar portion of the bolus. If the bolus is bent near the collar portion, the stylet may pierce the tube. On the other hand, if the length of the stylet is within the longer dimension range and the length of the tube is within the shorter dimension range, the stylet may be positioned within the fluid opening. In this situation, the stylet may pass through the fluid opening if the bolus is bent or kinked.

It is therefore an object of the present invention to provide a bolus for an enteral feeding tube that provides delivery of fluid to a body cavity or aspiration of a body cavity that does not become occluded with mucous, gastrointestinal debris and coagulated feeding material.

It is also an object of the present invention to provide a bolus for an enteral feeding tube that approximates the fluid flow rate characteristics of an open-ended tube.

It is also an object of the present invention to provide a bolus for an enteral feeding tube that has an elongated collar portion and a fluid outlet that is biased toward the distal end of the bolus to allow for greater tolerances between the lengths of the stylet and tube while preventing a shorter length stylet from piercing the tube or a longer length stylet from passing through the fluid outlet if the bolus is bent or kinked.

It is also an object of the present invention to provide a single bolus that can be used in more than one intubation procedure, including an over-the-wire procedure, by providing a stylet passage at the bolus tip while maintaining a generally contoured tip to promote travel through tortuous anatomy.

These and other objects of the present invention will become readily apparent after review of the specification and accompanying drawings.

SUMMARY OF THE INVENTION

The present invention is a bolus for an enteral feeding tube, or catheter, that is capable of being used in an over-the-wire intubation procedure as well as other intubation procedures. The bolus has a generally tubular body defining a sidewall, a proximal end tube opening capable of being connected to a distal end of the enteral feeding tube, and a generally rounded terminal end having a flattened tip. The bolus includes a fluid opening within the sidewall of the bolus between the proximal end opening and the terminal end of the bolus. The fluid opening is biased toward the terminal end of the bolus thereby defining an elongated collar portion adjacent the proximal end tube opening of the bolus. The terminal end of the bolus has an aperture therethrough that forms a stylet passage in communication with the fluid opening. The stylet passage is sized to allow a stylet to pass therethrough when the tube is used in an over-the-wire intubation procedure.

The fluid opening includes a distal end and defines edge surfaces of the side wall of the bolus that converge and curve upwardly at the distal end of the opening near the terminal end of the bolus. Furthermore, an interior surface of the sidewall opposite the fluid opening is curved and slopes upwardly toward the distal end of the fluid opening. The curved interior surface and the fluid opening configuration allow for fluid flow that approximates the fluid flow rate characteristics of an open-ended tube.

Additional features and advantages of the present invention are described in, and will be apparent from, the following Detailed Description of the Invention and the figures.

DETAILED DESCRIPTION OF THE INVENTION

While the present invention will be described fully hereinafter with reference to the accompanying drawings, in which a particular embodiment is shown, it is to be understood at the outset that persons skilled in the art may modify the invention herein described while still achieving the desired result of this invention. Accordingly, the description which follows is to be understood as a broad informative disclosure directed to persons skilled in the appropriate arts and not as limitations of the present invention.

It should also be understood that while the description is made herein with reference to an enteral feeding tube, this description is by way of example only. The principles of the present invention may be applied to all types of catheter tubes, including Foley catheters, urethral catheters, and catheters for use in gastric, esophageal, pharyngeal, nasal, intestinal, rectalcolonic, choledochal, arterial, venous, cardiac and endobronchial applications.

Figure 1:
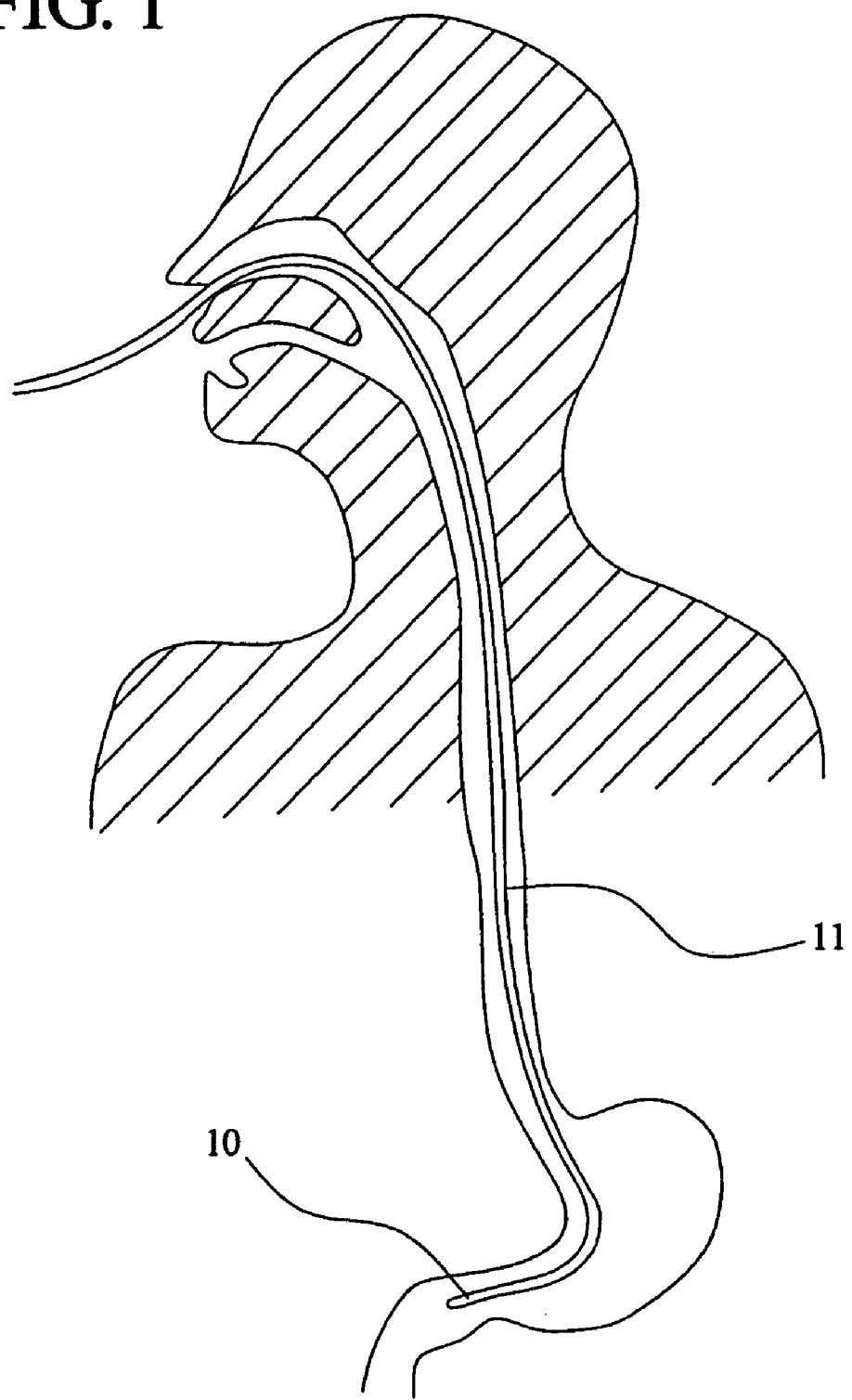
FIG. 1 is an illustration depicting an intubation configuration for an enteral feeding tube in a patient.
Figure 2:
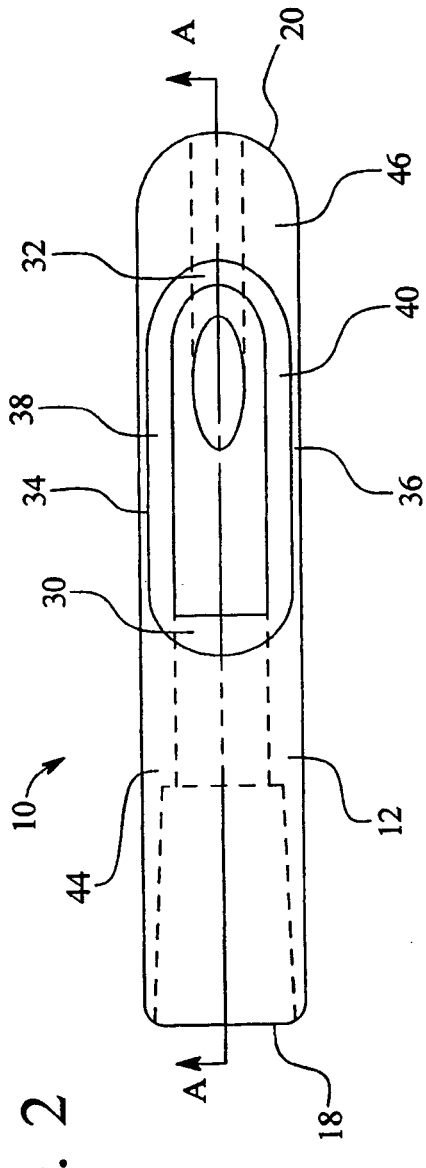
FIG. 2 is a plan view of a bolus of the present invention.
Figure 3:
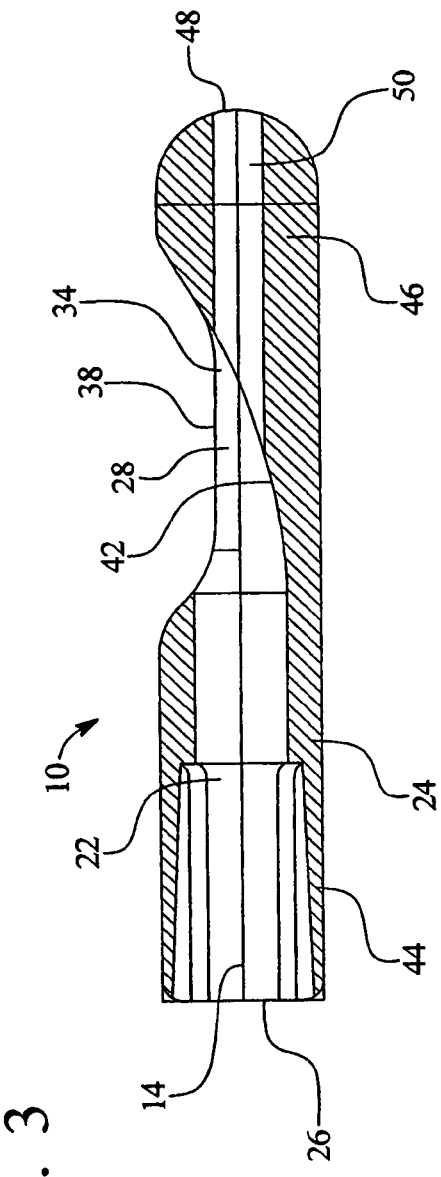
FIG. 3 is a cross-sectional view of the bolus depicted in FIG. 2 taken along section line A—A.

Referring to FIGS. 1–3, the present invention is a bolus 10 adapted to be connected to a distal end of an enteral feeding tube 11, as shown in FIG. 1. The bolus 10 can also be connected to the end of a catheter (not shown) for irrigation and aspiration of fluids within various body cavities of a patient. The bolus 10 has a generally tubular, or cylindrical, body 12 having a center axis 14. The body 12 includes a proximal end 18 and a distal, or terminal, end 20. The terminal end 20 is generally rounded and has a flattened tip configuration, as shown in FIGS. 2 and 3. The rounded configuration helps the bolus 10 to travel through tortuous anatomy, such as the gastrointestinal tract. The body 12 also includes a fluid passage 22 disposed within the body 12. The fluid passage 22 defines a bolus sidewall 24 and a proximal end tube opening 26. The tube opening 26 is adapted to be connected to, and in fluid communication with, a distal end of the enteral feeding tube 11, as shown in FIG. 1.

The fluid passage 22 diverges from the center axis 14 of the body 12 to define a fluid opening 28 through the sidewall 24, as shown in FIG. 3. The fluid opening 28 defines a proximal opening end 30, a distal opening end 32 and two generally vertical sidewalls 34 and 36 of the sidewall 24. The sidewalls 34 and 36 have edge surfaces 38 and 40, respectively. The edge surfaces 38 and 40 converge and curve upwardly at the distal end 32 of the opening 28. The edge surfaces 38 and 40 also curve upwardly adjacent to the proximal opening end 30, as shown in FIG. 3. An interior surface 42 of the sidewall 24 opposite the fluid opening 28 is curved and slopes upwardly toward the distal end 32 of the fluid opening 28. The interior surface 42 and the curved edge surfaces 38 and 40 of the fluid opening 28 allows for fluid flow that approximates the fluid flow rate characteristics of an open-ended tube.

The fluid opening 28 is biased toward the distal end 20 of the body 12, thereby defining an elongated collar portion 44 near the proximal end 18 of the body 12. The fluid opening also defines a distal end portion 46. The distal end 20 of the body 12 has an aperture 48 therethrough that forms a stylet passage 50 through the distal end portion 46 in communication with the fluid opening 28, as shown in FIG. 3. The stylet passage 50 is sized to allow a stylet (not shown) to pass therethrough when the tube is used in an over-the-wire intubation procedure. In a preferred embodiment, the stylet passage 50 has a diameter that is relatively smaller than a diameter of the fluid passage 28. Thus, the distal end portion 46 has a thicker material configuration than that of the sidewall 24 of the collar portion 44 of the body 12. The thick material provides rigidity to the distal end 20 of the body 12 and helps the bolus to travel through the gastrointestinal tract during the intubation procedure.

The overall lengths of a wire stylet (not shown) and tube (not shown) are subject to certain assembly tolerances. The elongated collar portion 44 and the forward-biased, or distal-biased, fluid opening 28 effectively allow for increased tolerances between the length of a wire stylet disposed within the enteral tube of an enteral tube/stylet assembly. The longer collar portion 44 creates a larger dimensional range in which a distal end of the wire stylet may be positioned while not falling short of the collar portion 44 or extending past the collar portion 44 and thereby residing within the fluid passage 22 at the fluid opening 28. The elongated collar portion 44 thereby prevents the stylet from piercing the tube adjacent to the collar portion 44 if the bolus is bent or kinked. The collar portion 44 also prevents the stylet from passing through the fluid opening 28 and potentially causing injury to the patient during intubation.

Figure 4:
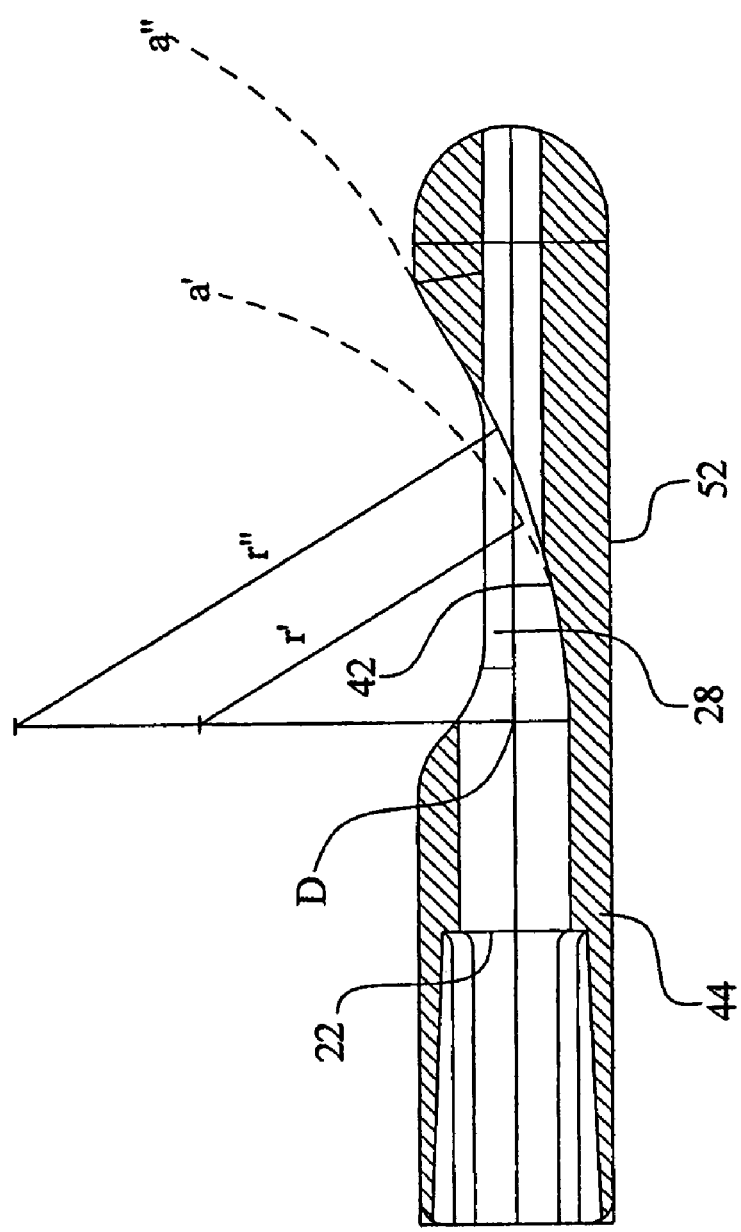
FIG. 4 is a cross-sectional view of the bolus depicted in FIG. 2 taken along section line A—A and depicting a range of curvatures of an interior surface of the bolus opposite a fluid opening.

The curved interior surface 42 is optimized to increase fluid flow through the fluid opening 28. FIG. 4 discloses a range of preferred curvatures of the curved interior surface 42. The curvature of the interior surface 36 is essentially a function of the inner diameter of the fluid passage 22 as characterized by a particular French size. The French size scale is most commonly used to describe the size of medical tubing such as enteral feeding tubing, urinary drainage tubing and catheters. The French scale (hereinafter "Fr.") is disclosed and compared against the American and English medical tubing size scales in Remington's Pharmaceutical Sciences (6th Ed. 1980; Mack Publishing Co.) pp. 1906–1907. Generally, the enteral feeding tubing employed in the present invention have French sizes from five to ten Fr. and are generally from 15 to 42 inches in length depending on whether the medical application is for neonatal, juvenile or adult patients.

The upward curvature of the interior surface 42 cannot be too severe otherwise obstruction of the fluid stream will result causing fluid turbulence and decreasing fluid flow output. On the other hand, the upward curvature of the interior surface 42 cannot be too shallow so as to require an overly long bolus to accommodate the more gradual incline.

FIG. 4 discloses curvatures for the interior surface 42 that maximize fluid flow rates. The selected range of curvatures is defined by arcs (a) circumscribed from radii (r) having lengths of between and including five times and ten times an inner diameter of the fluid passage 22 within the collar portion 44 and adjacent to the fluid opening 28, as indicated by the letter D in FIG. 4. In a preferred embodiment, the inner diameter D is equal to the inner diameter of the tubing. FIG. 4 generally discloses one end of the general range of preferred curvatures of the interior surface 42 in which an arc a' is circumscribed from a radius r' having a length equal to five times the inner diameter D. At the other end of the range of preferred curvatures, an arc a" is circumscribed from a radius r" having a length equal to ten times the inner diameter D.

In specific embodiments of the present invention, a six French enteral feeding tube having an inner diameter of about 0.055 inches requires the radius r defining the curvature of the interior surface 42 to have a length of about 0.489 inches or 8.890 times the inner diameter D. In an embodiment comprised of eight French enteral feeding tubing having an inner diameter of about 0.078 inches, the upward curvature of the interior surface 42 is defined by an arc circumscribed from a radius r having a length of 0.525 inches or 6.730 times the inner diameter D. In another specific embodiment of the present invention utilizing ten French enteral tubing having an inner diameter of 0.100 inches, the interior surface 42 was defined from an arc circumscribed from a radius having a length of 0.525 inches or 5.25 times the inner diameter D.

Another important feature of the present invention is the selective recessing or lowering of the height of the generally vertical side walls 34 and 36 defined by the fluid opening 28. A transverse sectional height is defined as the distance from an outside surface 52 of the sidewall 24 of the bolus 10 directly opposite the fluid opening to the edge surfaces 38 and 40. It has been found that the transverse sectional height of the vertical side walls 34 and 36 may range from a minimum height equal to one-half the inner diameter D. At a maximum, the transverse sectional height of the vertical side walls 34 and 36 should be no greater than the sum of the inner diameter D plus the thickness of the sidewall 24 of the bolus 10. The transverse sectional height may also be calculated in terms of the inner diameter of the tubing. In a preferred embodiment, the inner diameter D is equal to the inner diameter of the tubing. Therefore, in a preferred embodiment of the present invention, the transverse sectional height of the vertical side walls 34 and 36 is equal to about the inner diameter of the tubing.

If the transverse sectional height of the vertical side walls 34 and 36 is less than one half the inner diameter of the tubing, then bolus 10 has an increased tendency to kink or bend. On the other hand, if the vertical side walls 34 and 36 have a transverse sectional height greater than the sum of the inner diameter and thickness of the sidewall 22, this results in a vertical side wall height exceeding the outer configuration of bolus 10 thereby creating difficulty in intubation. Thus, the vertical side walls 34 and 36 are dimensioned to minimize kinking, bending, and occlusion of the fluid opening while maximizing fluid flow through the fluid opening. The present invention provides a versatile bolus for an enteral feeding tube, or catheter, that is capable of being used in an over-the-wire intubation procedure in addition to other intubation procedures. The bolus provides a stylet passage in combination with a generally rounded distal end having a blunt tip. The stylet passage allows the bolus to be used for an over-the-wire intubation procedure and the blunt tip allows the bolus to be inserted in an intubation procedure while maintaining minimal resistance and minimizing occlusion of the fluid opening.

While the specific embodiments have been illustrated and described, numerous modifications come to mind without significantly departing from the spirit of the invention and the scope of protection is only limited by the scope of the accompanying claims.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A catheter comprising:
   a tube having a plurality of ends; and
   a tip positionable within a bodily cavity, the tip having:
   (a) a collar member that defines an opening, the collar member having:
      (i) a length;
      (ii) a first end and a second end, the first end connected to one of the ends of the tube; and
      (iii) a bottom wall, a top wall and a plurality of side walls positioned between the first and second ends, the side walls connecting the top wall to the bottom wall;
   (b) an end member having:
      (i) a length that is less than the length of the collar member;
      (ii) a first end and a second end; and
      (iii) a bottom wall, a top wall and a plurality of side walls positioned between said first and second ends, said side walls connecting said top wall to the bottom wall of the end member; and
   (c) an intermediate section positioned between the collar member and end member, the intermediate section including another bottom wall and a plurality of lowered side walls, said another bottom wall and the lowered side walls being connected to the collar member and the end member, a portion of the lowered side walls and a portion of the top walls of both the collar member and the end member defining another opening having a center, the center of said opening positioned closer to the first end of the end member than the second end of the collar member.

2. The catheter of claim 1, wherein the second end of the end member has a partially rounded shape.

3. The catheter of claim 1, wherein the opening positioned between the second end of the collar member and the first end of the end member has an elongated shape.

4. The catheter of claim 1, wherein a portion of the bottom wall of the intermediate section has a sloped interior surface.

5. The catheter of claim 1, wherein a portion of the bottom wall of the intermediate section has an arc-shaped interior surface.

6. The catheter of claim 5, wherein: (a) the opening of the first end of the collar member has an inner diameter; and (b) said arc-shaped interior surface is defined by a radius, the radius having a magnitude within a range between and including five times and ten times said inner diameter.

7. The catheter of claim 1, wherein: (a) the opening of the first end of the collar member has an inner diameter; and (b) each of the lowered side walls of the intermediate section has a height that is selected from the group consisting of: (i) a height substantially equal to one-half of said inner diameter; (ii) a height equal to one-half of said inner diameter; and (iii) a height having a magnitude within a range between and including one-half of said inner diameter and said inner diameter.

8. The catheter of claim 1, wherein: (a) the tube has an inner diameter; and (b) each of the lowered side walls of the intermediate section has a height that is selected from the group consisting of: (i) a height substantially equal to one-half of said inner diameter; (ii) a height equal to one-half of said inner diameter; and (iii) a height having a magnitude within a range between and including one-half of said inner diameter and said inner diameter.

9. The catheter of claim 1, wherein the second end of the end member defines an opening sized to receive a wire.

10. A catheter comprising:
    a tube having a plurality of ends; and
    a tip having:
    (a) a collar member that defines an opening, the collar member having:
       (i) a length;
       (ii) a first end and a second end, the first end connected to one of the ends of the tube; and
       (iii) a bottom wall, a top wall and a plurality of side walls positioned between the first and second ends, the side walls connecting the top wall to the bottom wall;
    (b) an end member having:
       (i) a length that is less than the length of the collar member;
       (ii) a first end and a second end; and
       (iii) a bottom wall, a top wall and a plurality of side walls positioned between said first and second ends, said side walls connecting said top wall to the bottom wall of the end member; and
    (c) an intermediate section positioned between the collar member and the end member, the intermediate section including another bottom wall and a plurality of lowered side walls, said another bottom wall and the lowered side walls being connected to the collar member and the end member, a portion of the lowered side walls and a portion of the top walls of both the collar and the end member defining another opening having a center, the center of said opening being positioned closer to the first end of the end member than the second end of the collar member.

11. The catheter of claim 10, wherein the second end of the end member has a partially rounded shape.

12. The catheter of claim 10, wherein the opening positioned within the intermediate section has an elongated shape.

13. The catheter of claim 10, wherein a portion of the bottom wall of the intermediate section has a sloped interior surface.

14. The catheter of claim 10, wherein a portion of the bottom wall of the intermediate section has an arc-shaped interior surface.

15. The catheter of claim 14, wherein: (a) the opening of the first end of the collar member has an inner diameter; and (b) said arc-shaped interior surface is defined by a radius, the radius having a magnitude within a range between and including five times and ten times said inner diameter.

16. The catheter of claim 10, wherein: (a) the opening of the first end of the collar member has an inner diameter; and (b) each of the lowered side walls of the intermediate section has a height that is selected from the group consisting of: (i) a height substantially equal to one-half of said inner diameter; (ii) a height equal to one-half of said inner diameter; and (iii) a height having a magnitude within a range between and including one-half of said inner diameter and said inner diameter.

17. The catheter of claim 10, wherein: (a) the tube has an inner diameter; and (b) each of the lowered side walls of the intermediate section has a height that is selected from the group consisting of: (i) a height substantially equal to one-half of said inner diameter; (ii) a height equal to one-half of said inner diameter; and (iii) a height having a magnitude within a range between and including one-half of said inner diameter and said inner diameter.

18. The catheter of claim 10, wherein the second end of the end member defines an opening sized to receive a wire.

19. A catheter comprising:
    a tube having a plurality of ends; and
    a tip positionable within a bodily cavity, the tip having:
    (a) a collar member that defines an opening, the collar member having:
       (i) a length;
       (ii) a first end and a second end, the first end connected to one of the ends of the tube; and
       (iii) a bottom wall, a top wall and a plurality of side walls positioned between the first and second ends, the side walls connecting the top wall to the bottom wall;
    (b) an end member having:
       (i) a length that is less than the length of the collar member;
       (ii) a first end and a second end, the second end having a partially rounded shape; and
       (iii) a bottom wall, a top wall and a plurality of side walls positioned between said first and second ends, said side walls connecting said top wall to the bottom wall of the end member; and
    (c) an intermediate section positioned between the collar member and end member, the intermediate section including another bottom wall and a plurality of lowered side walls, said another bottom wall and the lowered side walls being connected to the collar member and the end member, a portion of the lowered side walls and a portion of the top walls of both the collar member and the end member defining another opening, said opening having a center and an elongated shape, the center of said opening being positioned closer to the first end of the end member than the second end of the collar member.

20. The catheter of claim 19, wherein a portion of the bottom wall of the intermediate section has an arc-shaped interior surface.

21. The catheter of claim 20, wherein: (a) the opening of the first end of the collar member has an inner diameter; and (b) said arc-shaped interior surface is defined by a radius, the radius having a magnitude within a range between and including five times and ten times said inner diameter.

22. The catheter of claim 19, wherein: (a) the opening of the first end of the collar member has an inner diameter; and (b) each of the lowered side walls of the intermediate section has a height that is selected from the group consisting of: (i) a height substantially equal to one-half of said inner diameter; (ii) a height equal to one-half of said inner diameter; and (iii) a height having a magnitude within a range between and including one-half of said inner diameter and said inner diameter.

23. The catheter of claim 19, wherein: (a) the tube has a designated inner diameter; and (b) each of the lowered side walls of the intermediate section has a height that is selected from the group consisting of: (i) a height substantially equal to one-half of said inner diameter; (ii) a height equal to one-half of said inner diameter; and (iii) a height having a magnitude within a range between and including one-half of said inner diameter and said inner diameter.

24. The catheter of claim 19, wherein the second end of the end member defines an opening sized to receive a wire.

* * * * *